(12) United States Patent
Leveque et al.

(10) Patent No.: US 8,084,638 B2
(45) Date of Patent: Dec. 27, 2011

(54) SULFANYL DERIVATIVES AND THEIR USE AS SYNTHESIS INTERMEDIATES

(75) Inventors: Julien Leveque, Brussels (BE); Nicolas Barbarin, Brussels (BE); Magali Palacio, Brussels (BE)

(73) Assignee: UCB Pharma, S.A., Brussels (BE)

( * ) Notice: Subject to any disclaimer, the term of this patent is extended or adjusted under 35 U.S.C. 154(b) by 86 days.

(21) Appl. No.: 12/671,055

(22) PCT Filed: Jul. 17, 2008

(86) PCT No.: PCT/EP2008/059396
§ 371 (c)(1),
(2), (4) Date: May 26, 2010

(87) PCT Pub. No.: WO2009/019119
PCT Pub. Date: Feb. 12, 2009

(65) Prior Publication Data
US 2010/0292505 A1      Nov. 18, 2010

(30) Foreign Application Priority Data

Aug. 3, 2007 (EP) .................................... 07015316
Oct. 3, 2007 (EP) .................................... 07019390

(51) Int. Cl.
*C07C 309/13* (2006.01)
*C07C 309/07* (2006.01)
(52) U.S. Cl. ...................................................... 562/102
(58) Field of Classification Search ................... 562/102
See application file for complete search history.

(56) References Cited

U.S. PATENT DOCUMENTS 2,695,310 A    11/1954   Schramm et al.

FOREIGN PATENT DOCUMENTS

| WO | WO 98/14426 A | 4/1998 |
| WO | WO 02/06216 A | 1/2002 |
| WO | WO 2005/058005 A | 6/2005 |

OTHER PUBLICATIONS

Schramm C. H. et al.: "The synthesis of mercaptoalkanesulfonic acids," J. Am. Chem. Soc., vol. 77, No. 23, 1955, pp. 6231-6233.
Jary, Jiri et al.: "Method of 2-Mercaptoethane Sulfonic Acid Production," CAPLUS, Feb. 12, 1987.
Schramm, C. H. et al.: "The synthesis of mercaptoalkanesulfonic acids," J. Am. Chem. Soc., vol. 77, No. 23, 1955, pp. 6231-6233.

*Primary Examiner* — Peter O Sullivan
(74) *Attorney, Agent, or Firm* — McDonnell Boehnen Hulbert & Berghoff LLP

(57) ABSTRACT

The present application relates to sulfanyl derivatives of formula (I) and to their use as synthesis intermediates, especially for the preparation of the pharmaceutically active compound mesna. Formula (I), wherein X is O or N—C(NH)NH$_2$; M+ is hydrogen, sodium, disodium, potassium, dipotassium, ammonium (NH$_4$)+, diammonium, quaternary ammonium, calcium or magnesium.

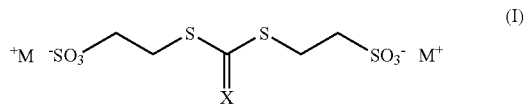

(I)

7 Claims, No Drawings

SULFANYL DERIVATIVES AND THEIR USE AS SYNTHESIS INTERMEDIATES

This application is a US national phase of International Application No. PCT/EP2008/059396 filed on Jul. 17, 2008.

The present invention relates to new sulfanyl derivatives and to their use as synthesis intermediates, especially for the preparation of pharmaceutically active compounds.

2-mercaptoethanesulfonic acid sodium salt (1:1) (HS CH$_2$CH$_2$SO$_3$Na), also known by the generic name of mesna (sodium 2-mercaptoethane sulfonate), has been proven useful as therapeutic agent for the treatment of some diseases; it is known as having mucolytic activity (U.S. Pat. No. 3,576,835); but also as antiviral agent, particularly as an anti-influenza agent (Patent EP 1 596 851 B). Topical use of mesna in surgical procedures that involve the dissection of tissues, is known (Patent EP0 930 878 B). Mesna protects the urinary tract from urotoxic symptoms in the treatment of tumour disease with ifosfamide (U.S. Pat. No. 6,322,812).

We have now found an alternative process for preparing mesna.

We have now found an improved process for preparing mesna, using a safe and economical route.

In a first aspect, the present invention relates to compounds of formula (I), and salts thereof,

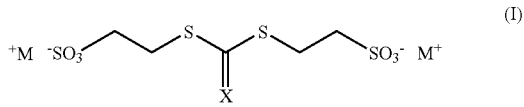

wherein
X is O or N—C(NH)NH$_2$;
M$^+$ is hydrogen, sodium, disodium, potassium, dipotassium, ammonium (NH$_4$)$^+$, diammonium, quaternary ammonium, calcium or magnesium.

Usually M$^+$ is hydrogen, sodium or disodium.

Usually the compounds of the invention are 2-(2-sulfoethylsulfanyl guanidinosulfanyl)-ethanesulfonic acid and salts thereof. Usually the compounds of the invention are also 2-(2-sulfo-ethylsulfanyl carbonylsulfanyl)-ethanesulfonic acid and salts thereof.

A preferred compound of the invention is the disodium salt of 2-(2-sulfo-ethylsulfanylguanidinosulfanyl)-ethanesulfonic acid ((C$_6$H$_{11}$N$_3$S$_4$O$_6$)$_2$Na$_2$).

Another preferred compound of the invention is the disodium salt of 2-(2-sulfo-ethylsulfanylcarbonylsulfanyl)-ethanesulfonic acid ((C$_5$H$_8$S$_4$O$_7$)$_2$Na$_2$).

Compounds of formula (I) can be in the form of a salt, any pharmaceutically acceptable salt; usually alkaline salt; preferably sodium, disodium, potassium, dipotassium, ammonium (NH$_4$)$^+$, diammonium, quaternary ammonium, calcium, magnesium. More preferably compounds of formula (I) are in the form of disodium salt.

Compounds of formula (I) are as follows:

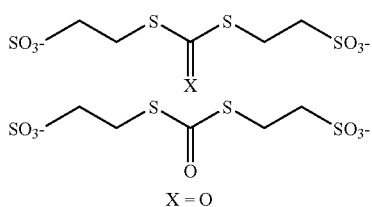

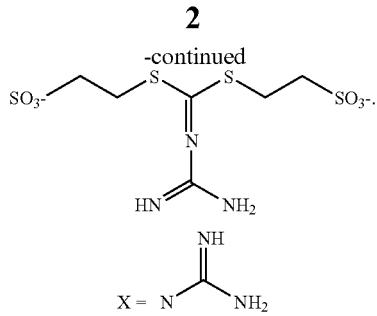

Compounds of formula (I) can be in the form of a solvate, which is included in the scope of the present invention. Such solvates include for example hydrates, alkoxides and the like.

Compounds of formula (I) are very stable and can be used as synthesis intermediates. In particular hydrolysis of the compounds of the invention gives mesna and dimesna.

Compounds of the invention may be obtained by coupling (ethyl xanthate) O-ethylester carbonodithio acid, potassium salt with (sodium 2 bromoethanesulphonate) 2-bromoethanesulfonic acid sodium salt to give ethyl-2-sulfoethylester xanthic acid sodium salt followed by a radical reaction to generate the disodium salt of 2-(2-sulfo-ethylsulfanylcarbonylsulfanyl)-ethanesulfonic acid. To obtain the disodium salt of 2-(2-sulfo-ethylsulfanylguanidinosulfanyl)-ethanesulfonic acid, guanidine is added in the above reaction medium.

In another aspect, the present invention relates to the use of compounds of general formula (I) as synthesis intermediates, especially for the preparation of pharmaceutically active compounds.

According to a first embodiment, compounds of formula (I) are used for the synthesis of mesna.

Mesna may be obtained by hydrolysis a compound of formula (I), followed by an isolation.

The use of compounds of general formula (I) as synthesis intermediates permits to produce mesna with high yield (at least 80%) and with high purity (at least 85%, usually more than 90% and preferably more than 95%), using a short and simple route and also mainly a safe and economical route.

The present invention will be better understood from the following examples which only serve to illustrate the invention. Those skilled in the art will appreciate that routine variations and modifications of the following examples can be made without exceeding the spirit or scope of the invention.

EXAMPLES

Example 1

Preparation of Ethyl-2-sulfoethylester Xanthic Acid Sodium Salt

Potassium O-ethylxanthate (3×95 mg, 0.60 mmol) is added portion wise every 1.5 hours to a solution of sodium 2-bromoethanesulphonate (0.42 g, 2.00 mmol) in acetonitrile (15 ml). The reaction mixture is heated at 85° C., under a nitrogen atmosphere, for a total of 6 hours. Upon cooling the suspension is filtered, washed with acetonitrile and air-dried affording an off-white solid.

$^1$H NMR (DMSO d6) δ (ppm) 4.67 (q, 2H), 3.40 (2H, m), 3.26 (m, 2H), 1.39 (t, 3H).

Example 2

Preparation of Disodium Salt of 2-(2-sulfo-ethylsulfanylcarbonylsulfanyl)-ethanesulfonic Acid Ethyl-2-sulfoethylester xanthic acid sodium salt, as obtained in example 1, (0.20 g, 0.79 mmol) is added to 1,2-dichloroethane (5 ml) and is heated under reflux (85° C.). Lauroyl peroxide is then added in portions (8×157 mg, 0.40 mmol) to the reaction mixture over a period of 3 days. Upon cooling the resulting solid is filtered, washed with 1,2-dichloroethane, followed by dichloromethane, then air-dried.

The solid above mentioned (100 mg, 0.28 mmol) is suspended in ethanol (5 ml) and heated under gentle reflux (compound stable by $^1$H NMR analysis). Water (~0.5 ml) is then added to give complete solution, and reflux is continued for 2 h (compound stable by $^1$H NMR analysis). The solution is allowed to cool overnight to give a suspension which is filtered. The white solid is washed with cold ethanol (1 mL) and suction-dried to give the purified compound, 75 mg (75% recovery). The compound is pure by $^1$H NMR analysis.

Melting point: 284.8° C.
1H NMR (DMSO d6) δ (ppm) 3.26 (4H, m), 3.08 (4H, m)
13C NMR (DMSO d6) δ (ppm) 51.4, 26.8

Example 3

Preparation of Mesna from the Compound Obtained in Example 2

The compound obtained in example 2 (2 g, 5.65 mmol) is dissolved in 1N aqueous sodium hydroxide (20 ml, 20 mmol) and is stirred at room temperature under a nitrogen atmosphere. The resulting reaction mixture is heated at 80° C. for 3 hours. After this time the reaction mixture is allowed to cool before the excess solvent is removed by evaporation under reduced pressure. The resulting white solid is then triturated with ethanol (40 ml), under a nitrogen atmosphere, to give a white suspension to which glacial acetic acid (2.4 ml) is then added. After stirring for 5 minutes, the suspension is then quickly filtered, washed with ethanol (20 ml) and briefly suction-dried. The resulting white solid is then dried in vacuum (40° C.) for 30 minutes to give mesna as a white solid, 2.0 g, containing only minor impurities by $^1$H NMR (less than 0.1%).

This process leads to an active ingredient, mesna, of high purity profile.

The starting material (ethyl-2-sulfoethylester xanthic acid sodium salt) is safe and easy to use. In fact its use does not require specific precautions, as it is not an explosive compound. Mainly this process allows to avoid using dangerous synthesis intermediates such as thiourea and sulfo-ethyl-thiourea.

1H NMR (DMSO d6) δ (ppm) 3.26 (4H, m), 3.08 (4H, m).

Example 4

Preparation of Disodium Salt of 2-(2-sulfo-ethylsulfanylguanidinosulfanyl)-ethanesulfonic Acid The xanthic acid sodium salt, as obtained in example 1, (0.20 g, 0.79 mmol) is added to 1,2-dichloroethane (5 ml) and is heated under reflux (85° C.). Guanidine (1.25 eq.) is then added. Lauroyl peroxide is then added in portions (8×157 mg, 0.40 mmol) to the reaction mixture over a period of 3 days. Upon cooling the resulting solid is filtered, washed with 1,2-dichloroethane, followed by dichloromethane, then air-dried.

Example 5

Preparation of Mesna from the Compound Obtained in Example 4

The compound obtained in example 4 is recrystallized according to the process described in example 2. The obtained compound leads to mesna by following the process of preparation described in example 3.

The invention claimed is:
1. Compounds of formula (I), and salts thereof,

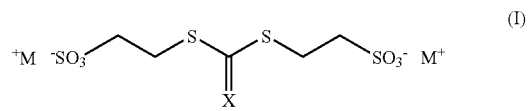

wherein
X is O or N—C(NH)NH$_2$;
M$^+$ is hydrogen, sodium, disodium, potassium, dipotassium, ammonium (NH$_4$)$^+$, diammonium, quaternary ammonium, calcium or magnesium.

2. The compound according to claim 1 wherein X is N—C(NH)NH$_2$.

3. The compound according to claim 1 wherein X is O.

4. The compound according to claim 1 wherein it is the disodium salt of 2-(2-sulfo-ethylsulfanylguanidinosulfanyl)-ethanesulfonic acid.

5. The compound according to claim 1 wherein it is the disodium salt of 2-(2-sulfo-ethylsulfanylcarbonylsu-lfanyl)-ethanesulfonic acid.

6. The compound according to claim 2 wherein it is the disodium salt of 2-(2-sulfo-ethylsulfanylguanidinosulfanyl)-ethanesulfonic acid.

7. The compound according to claim 3 wherein it is the disodium salt of 2-(2-sulfo-ethylsulfanylcarbonylsu-lfanyl)-ethanesulfonic acid.

* * * * *